(12) United States Patent
Abe

(10) Patent No.: US 11,703,484 B2
(45) Date of Patent: Jul. 18, 2023

(54) SENSOR MODULE

(71) Applicant: KYOCERA Corporation, Kyoto (JP)

(72) Inventor: Shinichi Abe, Uji (JP)

(73) Assignee: KYOCERA Corporation, Kyoto (JP)

(*) Notice: Subject to any disclaimer, the term of this patent is extended or adjusted under 35 U.S.C. 154(b) by 437 days.

(21) Appl. No.: 16/634,529

(22) PCT Filed: Jul. 24, 2018

(86) PCT No.: PCT/JP2018/027727
§ 371 (c)(1),
(2) Date: Jan. 27, 2020

(87) PCT Pub. No.: WO2019/022081
PCT Pub. Date: Jan. 31, 2019

(65) Prior Publication Data
US 2020/0173967 A1 Jun. 4, 2020

(30) Foreign Application Priority Data
Jul. 28, 2017 (JP) ................. 2017-147154

(51) Int. Cl.
G01N 1/00 (2006.01)
G01N 30/28 (2006.01)
G01N 30/04 (2006.01)
G01N 33/00 (2006.01)
G01N 30/02 (2006.01)
G01N 30/30 (2006.01)

(52) U.S. Cl.
CPC ............. *G01N 30/28* (2013.01); *G01N 30/04* (2013.01); *G01N 33/0009* (2013.01); *G01N 2001/002* (2013.01); *G01N 2030/025* (2013.01); *G01N 2030/3046* (2013.01)

(58) Field of Classification Search
CPC .................................... G01N 2001/002
See application file for complete search history.

(56) References Cited

U.S. PATENT DOCUMENTS

| | | | | |
|---|---|---|---|---|
| 3,039,053 A | * | 6/1962 | Jacobson | G01N 1/34 436/124 |
| 3,425,807 A | * | 2/1969 | Levy | G01N 31/12 422/89 |
| 9,417,207 B2 | | 8/2016 | Marra et al. | |
| 2003/0054576 A1 | * | 3/2003 | Ryu | H01L 22/26 257/E21.528 |
| 2010/0262034 A1 | | 10/2010 | Kawata et al. | |
| 2014/0377146 A1 | * | 12/2014 | Putnam | B01L 3/502707 422/505 |

FOREIGN PATENT DOCUMENTS

| | | |
|---|---|---|
| CN | 103649738 A | 3/2014 |
| JP | H02-115765 A | 4/1990 |
| JP | H04-131736 A | 5/1992 |
| JP | 2010-249556 A | 11/2010 |
| WO | WO-2014069551 A1 * 5/2014 | ........ B01L 3/502715 |

\* cited by examiner

Primary Examiner — Jamel E Williams
Assistant Examiner — Alex T Devito
(74) Attorney, Agent, or Firm — Studebaker & Brackett PC

(57) ABSTRACT

A sensor module includes a sensor configured to detect a specific substance in a sample, a first channel, and a second channel The first channel supplies a first fluid as the sample to the sensor. The second channel supplies a second fluid different from the first fluid to the sensor. The second channel includes a second fluid buffer tank for holding the second fluid for a fixed time interval.

11 Claims, 4 Drawing Sheets

SENSOR MODULE

CROSS REFERENCE TO RELATED APPLICATION

This application claims priority to and the benefit of Japanese Patent Application No. 2017-147154 filed on Jul. 28, 2017, the entire contents of which are incorporated herein by reference.

TECHNICAL FIELD

The present disclosure relates to a sensor module.

BACKGROUND

Conventionally, sensor modules for detecting a specific substance in a fluid are known. For example, PTL 1 discloses a gas component detection apparatus that includes a gas inlet and a gas detection unit.

CITATION LIST

Patent Literature

PTL 1: JP-A-2010-249556

SUMMARY

A sensor module according to an embodiment of the present disclosure includes a sensor configured to detect a specific substance in a sample, a first channel, and a second channel The first channel supplies a first fluid as the sample to the sensor. The second channel supplies a second fluid different from the first fluid to the sensor. The second channel includes a second fluid buffer tank for holding the second fluid for a fixed time interval.

DETAILED DESCRIPTION

Conventionally, it is desired to improve the measurement accuracy of a detection target substance by a sensor module. The present disclosure aims to provide a sensor module that improves a measurement accuracy of a detection target substance. A sensor module according to an embodiment of the present disclosure can improve a measurement accuracy of a detection target substance. Hereinafter, embodiments of the present disclosure will be described with reference to the drawings.

First Embodiment

Figure 1:
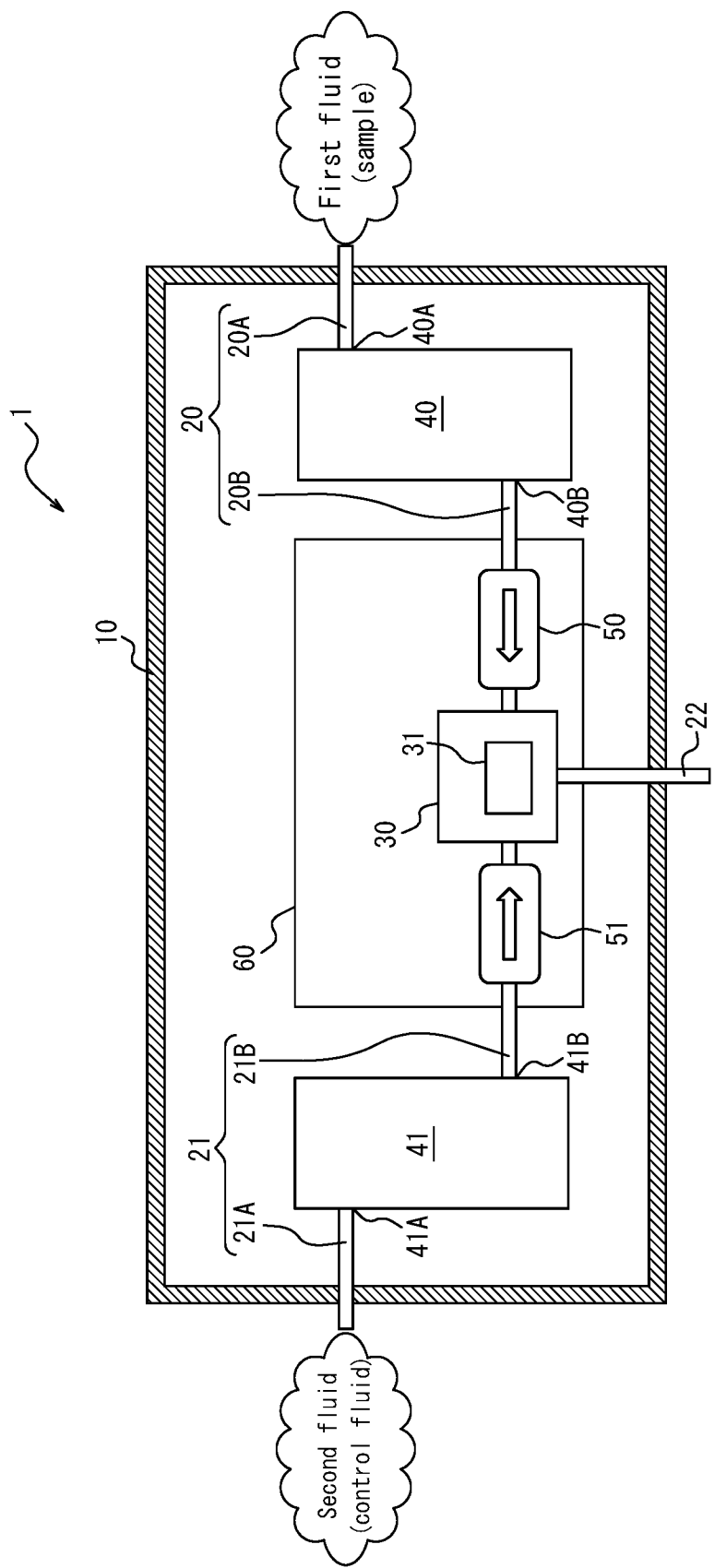
FIG. 1 is a schematic diagram illustrating a sensor module according to a first embodiment of the present disclosure.

FIG. 1 is a schematic diagram of a sensor module 1 according to a first embodiment of the present disclosure. The sensor module 1 includes a housing 10. FIG. 1 illustrates an interior of the housing 10 from which a portion of a surface is removed.

The sensor module 1 receives a first fluid as a sample and a second fluid different from the first fluid from the outside. The sensor module 1 detects a specific substance in the first fluid.

The first fluid is the sample. The first fluid is also referred to as a sample gas. For example, the first fluid is, but is not limited to, a biological gas (e.g., human breath), an odor, or a gas generated by heating or a chemical reaction. When the first fluid is human breath, the specific substance to be detected is, but is not limited to, acetone, ethanol, or carbon monoxide.

The second fluid is a control fluid. The second fluid is also referred to as a refresh gas, a purge gas, or a carrier gas, depending on the usage. For example, when the first fluid is human breath, the second fluid is, but is not limited to, air or nitrogen gas.

The sensor module 1 includes a first channel 20, a second channel 21, a discharge path 22, a chamber 30, and a circuit board 60, within the housing 10.

The first channel 20 supplies the first fluid to the chamber 30 from the outside. The first channel 20 includes a buffer tank 40 for the first fluid, and a first supply unit 50. The first channel 20 includes, for example, an inlet 20A and a passage 20B. The first channel 20 may further include a filter for reducing noise components contained in the first fluid.

The first fluid flows into the inlet 20A from the outside. The first fluid having flowed into the inlet 20A is supplied to the buffer tank 40. The inlet 20A is configured as, for example, a resin tube or a cylindrical member such as a metal or glass pipe. For example, one end of the inlet 20A extends to the outside of the housing 10. An inflow port that opens to the outside may be provided at one end of the inlet 20A. The other end of the inlet 20A is joined to the buffer tank 40.

The passage 20B supplies the first fluid held in the buffer tank 40 to the chamber 30 via the first supply unit 50. The passage 20B is configured as, for example, a resin tube or a cylindrical member such as a metal or glass pipe. For example, one end of the passage 20B is joined to the buffer tank 40. The other end of the passage 20B is joined to the chamber 30.

The second channel 21 supplies the second fluid to the chamber 30 from the outside. The second channel 21 includes a buffer tank 41 for the second fluid, and a second supply unit 51. The second channel 21 includes, for example, an inlet 21A and a passage 21B. The second channel 21 may further include a filter for reducing noise components contained in the second fluid.

The second fluid is flown into the inlet 21A from the outside. The second fluid having flowed into the inflow section 21A is supplied to the buffer tank 41. The inlet 21A is configured as, for example, a resin tube or a cylindrical member such as a metal or glass pipe. For example, one end of the inlet 21A extends to the outside of the housing 10. An inflow port that opens to the outside may be provided at one end of the inlet 21A. The other end of the inlet 21A is joined to the buffer tank 41.

The passage 21B supplies the second fluid held in the buffer tank 41 to the chamber 30 via the second supply unit 51. The passage 21B is configured as, for example, a resin tube or a cylindrical member such as a metal or glass pipe. For example, one end of the passage 21B is joined to the buffer tank 41. The other end of the passage 21B is joined to the chamber 30.

The discharge path 22 discharges exhaust from the chamber 30 to the outside. The exhaust includes, for example, the first fluid and the second fluid subjected to a detection process. The discharge path 22 is configured as, for example, a resin tube or a cylindrical member such as a metal or glass pipe.

The passage 20B of the first channel 20 is joined to the chamber 30. The chamber 30 receives the first fluid supplied from the passage 20B. The passage 21B of the second channel 21 is joined to the chamber 30. The chamber 30 receives the second fluid supplied from the passage 21B. The discharge path 22 is joined to the chamber 30. The chamber 30 discharges the first fluid and the second fluid subjected to the detection process from the discharge path 22. The chamber 30 includes a sensor 31 arranged therein.

The sensor 31 is arranged within the chamber 30. The sensor 31 includes a plurality of reaction units. Each of the reaction units may be configured as, for example, a film. The reaction units are responsive to specific substances. At least one of the plurality of reaction units are responsive to a component of a detection target substance. That is, at least one of the plurality of reaction units detects the detection target substance. The reaction units are deformed by adsorption of the specific substance contained in a fluid. The reaction units are formed from, for example, polystyrene, chloroprene rubber, polymethyl methacrylate, nitrocellulose, silicone resin, or fluorine resin. Each of the reaction units outputs a signal corresponding to a reaction with the specific substance. This signal is output as, for example, a voltage value.

The buffer tank 40 is located, for example, on the side for supplying the first fluid. The buffer tank 40 includes an inlet 40A through which the first fluid is introduced and an outlet 40B through which the first fluid flows out. The first fluid is supplied to the buffer tank 40 via the inlet 40A from the inlet 20A. The buffer tank 40 holds the first fluid for a fixed time interval. For example, the distance between the inlet 40A and the outlet 40B may be determined to be a predetermined length or more, such that the buffer tank 40 can hold the first fluid for the fixed time interval. Alternatively, the capacity of the buffer tank 40 may be determined to be a predetermined value or more, such that the buffer tank 40 can hold the first fluid for the fixed time interval. The buffer tank 40 may be configured as a bag-like tank or a cylindrical tank. The buffer tank 40 may be provided with a heater for heating the first fluid.

The buffer tank 40 holds the first fluid for the fixed time interval and then supplies the first fluid to the chamber 30 from the outlet 40B. Holding the first fluid in the buffer tank 40 for the fixed time interval homogenizes the components contained in the first fluid within the buffer tank 40. The temperature of the first fluid can also be homogenized within the buffer tank 40. Thus, the first fluid with components and temperature homogenized within the buffer tank 40 can be supplied to the chamber 30.

The buffer tank 41 is located, for example, on the side for supplying the second fluid. The buffer tank 41 includes an inlet 41A through which the second fluid is introduced and an outlet 41B through which the second fluid flows out. The second fluid is supplied to the buffer tank 41 via the inlet 41A from the inlet 21A. The buffer tank 41 holds the second fluid for a fixed time interval. For example, the distance between the inlet 41A and the outlet 41B may be determined to be a predetermined length or more, such that the buffer tank 41 can hold the second fluid for the fixed time interval. Alternatively, the capacity of the buffer tank 41 may be determined to be a predetermined value or more, such that the buffer tank 41 can hold the second fluid for the fixed time interval. The buffer tank 41 may be configured as a bag-like tank or a cylindrical tank. The buffer tank 41 may be provided with a heater for heating the second fluid.

The buffer tank 41 holds the second fluid for the fixed time interval and then supplies the second fluid to the chamber 30 from the outlet 41B. Holding the second fluid in the buffer tank 41 for the fixed time interval homogenizes the components contained in the second fluid within the buffer tank 41. The temperature of the second fluid can also be homogenized within the buffer tank 41. Thus, the second fluid with components and temperature homogenized within the buffer tank 41 can be supplied to the chamber 30.

The first supply unit 50 is installed to the passage 20B. The first supply unit 50 supplies the first fluid held in the buffer tank 40 to the chamber 30. The arrow illustrated in the first supply unit 50 indicates a direction in which the first supply unit 50 sends the first fluid. The first supply unit 50 is configured as, for example, a piezoelectric pump.

The second supply unit 51 is installed to the passage 21B. The second supply unit 51 supplies the second fluid held in the buffer tank 41 to the chamber 30. The arrow illustrated in the second supply unit 51 indicates a direction in which the second supply unit 51 sends the second fluid. The second supply unit 51 is configured as, for example, a piezoelectric pump.

The circuit board 60 packages wiring for propagating electrical signals, and a controller 62 and a memory 61 of the sensor module 1, which will be described later.

Figure 2:
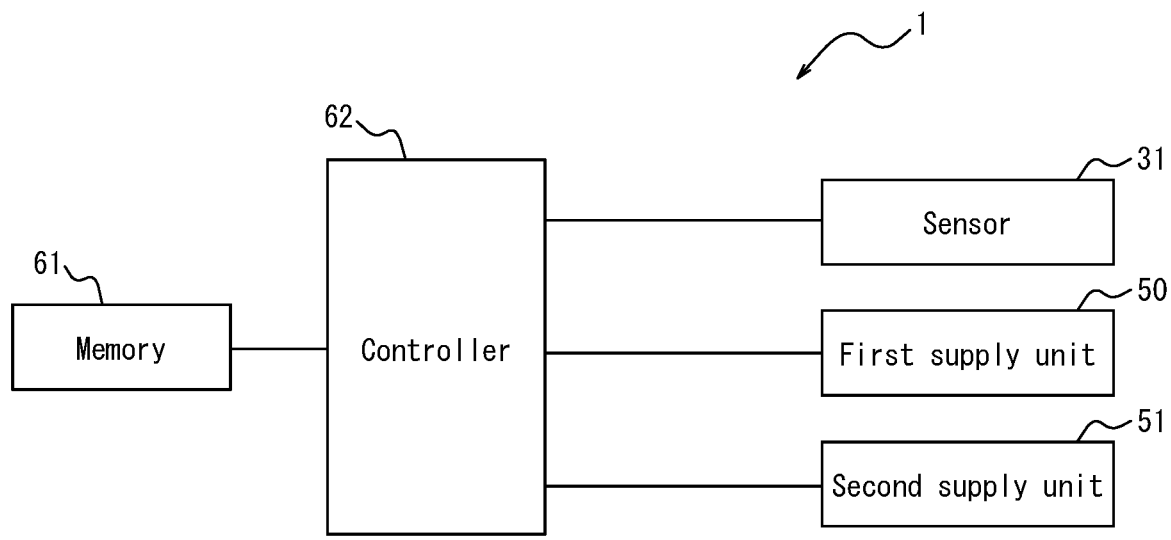
FIG. 2 is a functional block diagram illustrating a schematic configuration of the sensor module of FIG. 1.

FIG. 2 is a functional block diagram illustrating a schematic configuration of the sensor module 1 of FIG. 1. The sensor module 1 includes the sensor 31, the first supply unit 50, the second supply unit 51, the memory 61, and the controller 62.

The sensor 31 is arranged in the chamber 30, as described above. The sensor 31 outputs the signal from each of the reaction units to the controller 62.

The first supply unit 50 supplies the first fluid held in the buffer tank 40 illustrated in FIG. 1 to the chamber 30 at a predetermined timing, based on the control by the controller 62. The second supply unit 51 supplies the second fluid held in the buffer tank 41 illustrated in FIG. 1 to the chamber 30 illustrated in FIG. 1 at a predetermined timing, based on the control by the controller 62.

The memory 61 is configured as, for example, a semiconductor memory, a magnetic memory, or the like. The memory 61 is configured to store various information, a program for operating the sensor module 1, and the like. The memory 61 may function as a work memory.

The controller 62 is a processor configured to control and manage the entire sensor module 1 including each functional block thereof. The controller 62 is a processor such as a CPU (Central Processing Unit) configured to execute a program defining control procedure. Such a program is stored in, for example, the memory 61 or an external storage medium connected to the sensor module 1.

The controller 62 controls the first supply unit 50 and the second supply unit 51, such that the first fluid and the second fluid are alternately supplied to the chamber 30. By this control, while the first supply unit 50 supplies the first fluid to the chamber 30, the second supply unit 51 does not supply the second fluid to the chamber 30. Also, while the second supply unit 51 supplies the second fluid to the chamber 30, the first supply unit 50 does not supply the first fluid to the chamber 30.

While the first supply unit 50 supplies the first fluid to the chamber 30, the sensor 31 outputs a first signal corresponding to a component of the first fluid to the controller 62. Also, while the second supply unit 51 supplies the second fluid to the chamber 30, the sensor 31 outputs a second signal corresponding to a component of the second fluid to the controller 62. The controller 62 detects a specific substance contained in the first fluid, based on a difference between the first signal and the second signal received from the sensor 31.

In the sensor module 1 according to the first embodiment, as described above, the second fluid is held in the buffer tank 41 for the fixed time interval and then supplied to the chamber 30. This configuration can supply the second fluid having components and temperature homogenized within the buffer tank 41 to the chamber 30. Thus, the measurement accuracy of the detection target substance by the sensor module 1 can be improved, as will be described below.

As a comparative example, a sensor module which does not include a buffer tank 41 is assumed. In the sensor module according to the comparative example, the second fluid is directly supplied to the chamber 30 from the outside by the second supply unit 51 or the like. Here, component concentrations and temperature of the second fluid supplied from the outside may vary according to a change in a surrounding environment of the sensor module. For example, when air is used as the second fluid, humidity and temperature of the air in the room in which the sensor module is installed may vary by the influence of an air conditioner, a weather change, people entering or leaving the room, or the like, causing variations of the humidity and temperature of the second fluid. Because the sensor module according to the comparative example supplies the second fluid into the chamber 30 without processing, the variations of the component concentrations and temperature of the second fluid supplied from the outside causes variation of the component concentrations and temperature of the second fluid supplied to the chamber 30. The variation of the component concentrations and temperature of the second fluid supplied to the chamber 30 causes variation of a voltage value of the second signal corresponding to the component of the second fluid. The variation of the voltage value of the second signal makes it difficult to improve the measurement accuracy of the detection target substance.

In the first embodiment, on the other hand, even when the component concentrations and temperature of the second fluid supplied from the outside vary due to changes in the surrounding environment of the sensor module 1, the component concentrations and temperature of the second fluid can be homogenized within the buffer tank 41. Further, the second fluid with components and temperature homogenized within the buffer tank 41 can be supplied to the chamber 30. Thus, the sensor module 1 according to the present embodiment can stabilize the voltage value of the second signal corresponding to the component of the second fluid. According to the present embodiment, thus, the measurement accuracy of the detection target substance by the sensor module 1 can be improved.

Figure 3:
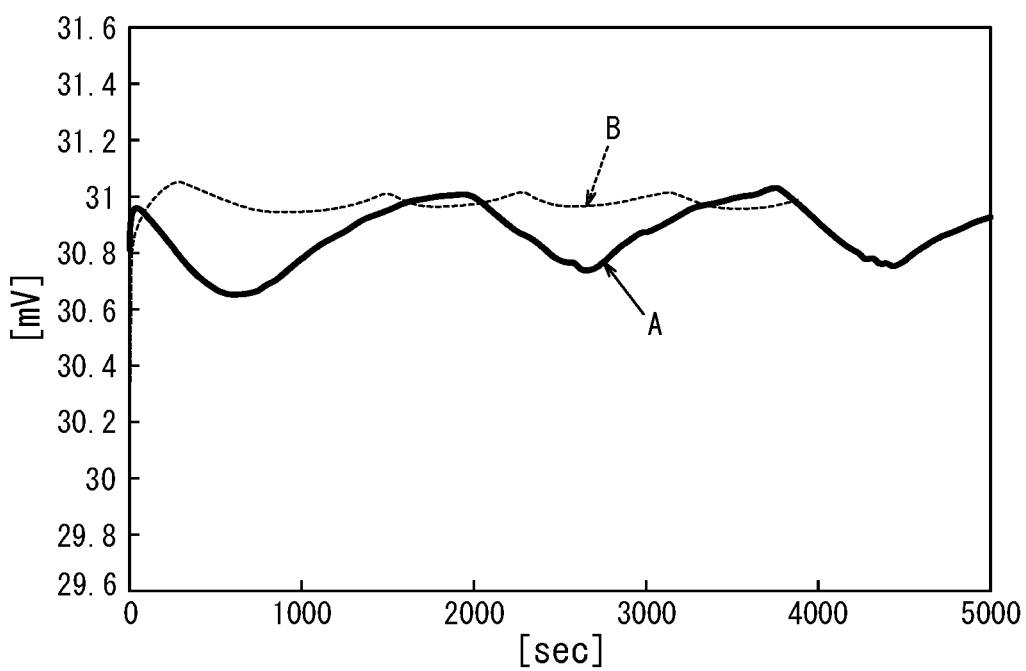
FIG. 3 is a diagram illustrating a waveform of a second signal corresponding to a component of a second fluid.

FIG. 3 illustrates a waveform of the second signal corresponding to the component of the second fluid. In FIG. 3, the vertical axis represents a voltage, and the horizontal axis represents time. Air within the room was used as the second fluid in FIG. 3. A waveform A indicates a second signal of the sensor module according to the comparative example A waveform B indicates the second signal of the sensor module 1 according to the first embodiment. In the sensor module according to the comparative example, the voltage value of the waveform A varies under the influence of an air conditioner. In the sensor module 1 according to the first embodiment, on the other hand, the voltage value of the waveform B is stable. According to the present embodiment, thus, the measurement accuracy of the detection target substance by the sensor module 1 can be improved.

Also, the sensor module 1 according to the first embodiment includes the buffer tank 40 for holding the first fluid for the fixed time interval. Here, when the first fluid is human breath, a concentration of a component contained in the first fluid may vary, depending on the timing at which the person exhales. Also, air in the room in which the sensor module 1 is disposed may be mixed into the first fluid. In such a case also, the present embodiment can homogenize the component concentration and temperature of the first fluid within the buffer tank 40. Further, the first fluid having the component concentration and temperature homogenized within the buffer tank 40 can be supplied to the chamber 30. Thus, the sensor module 1 according to the present embodiment can stabilize the voltage value of the first signal corresponding to the component of the first fluid. According to the present embodiment, thus, the measurement accuracy of the detection target substance by the sensor module 1 can be improved.

The sensor module 1 according to the first embodiment includes the buffer tank 40 for the first fluid and the buffer tank 41 for the second fluid. This configuration can homogenize the temperature of the first fluid and the temperature of the second fluid within the buffer tank 40 and the buffer tank 41, respectively, in a similar manner. Further, the first fluid and the second fluid having the respective temperature homogenized in the similar manner can be supplied to the chamber 30. Thus, a difference between the first signal corresponding to the component of the first fluid and the second signal corresponding to the component of the second fluid can more clearly correspond to the concentration of the detection target substance contained in the first fluid. According to the present embodiment, thus, the measurement accuracy of the detection target substance by the sensor module 1 can be improved.

Second Embodiment

Figure 4:
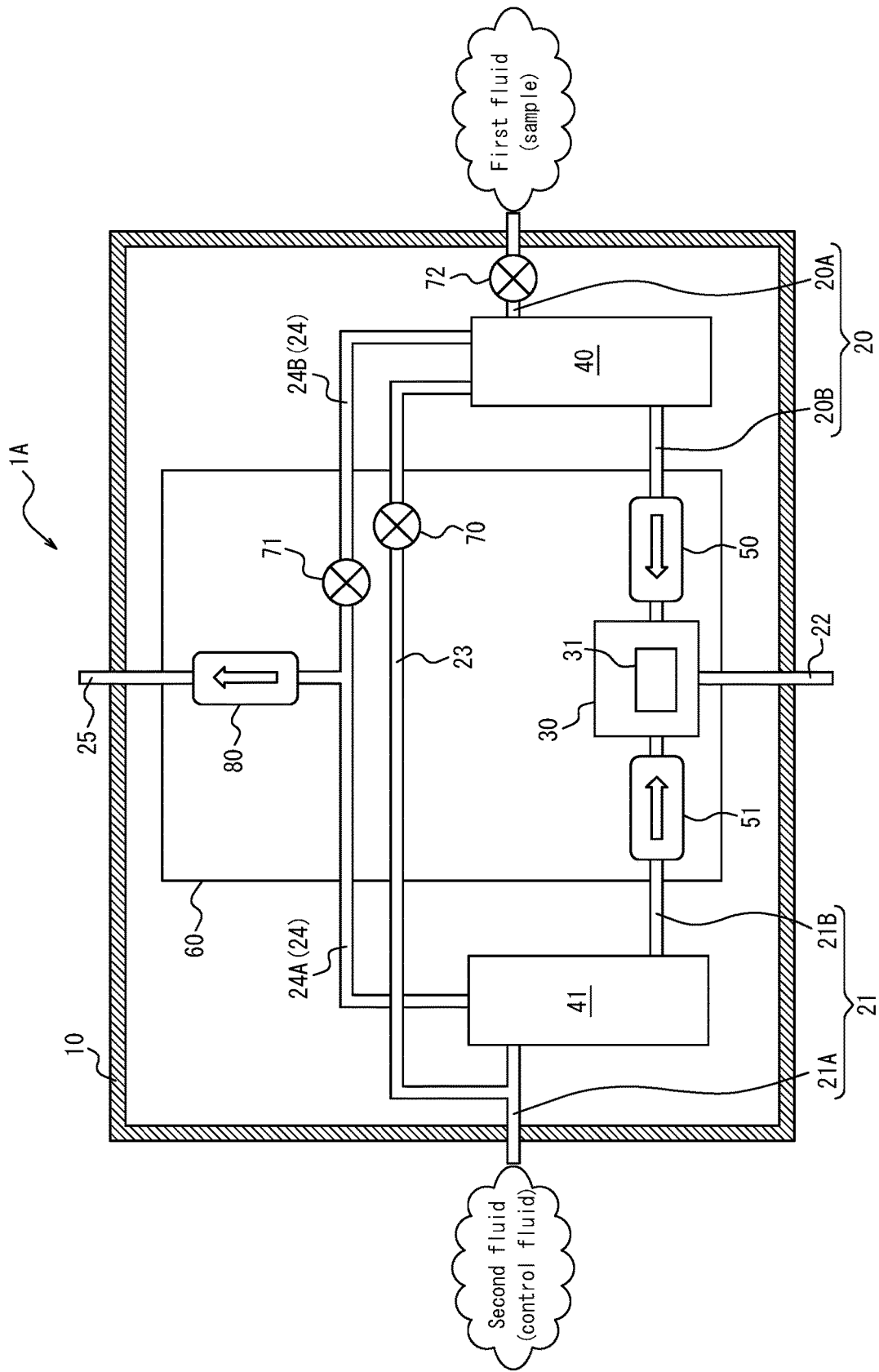
FIG. 4 is a schematic diagram illustrating a sensor module according to a second embodiment of the present disclosure.

FIG. 4 is a schematic diagram illustrating a sensor module 1A according to a second embodiment of the present disclosure. The constituent elements illustrated in FIG. 4 that are the same as those illustrated in FIG. 1 are denoted by the same reference signs, and descriptions thereof will be omitted.

The sensor module 1A according to the second embodiment discharges the sample remaining in the sensor module 1A to the outside of the sensor module 1A using the second fluid in a refresh process. The term "refresh process" as used herein refers to an operation to discharge the sample that was used in a previous detection process and remains in the sensor module 1A to the outside of the sensor module 1A, prior to detection of a specific substance contained in a next sample.

The sensor module 1A includes, within the housing 10, the first channel 20, the second channel 21, the discharge path 22, the third channel 23, the fourth channel 24, the fifth channel 25, the chamber 30, and the circuit board 60. The third channel 23 has a valve 70. The fourth channel 24 has a valve 71. The inlet 20A of the first channel 20 has a valve 72. The fifth channel 25 has a discharge unit 80.

The third channel 23 couples the second channel 21 and the buffer tank 40 for the first fluid. For example, one end of the third channel 23 is joined to the inlet 21A. The other end of the third channel 23 is joined to the buffer tank 40 for the second fluid. The third channel 23 is configured as, for example, a resin tube or a cylindrical member such as a metal or glass pipe.

The fourth channel 24 couples the buffer tank 40 for the first fluid and the buffer tank 41 for the second fluid. For example, one end of the fourth channel 24 is joined to the buffer tank 40. The other end of the fourth channel 24 is joined to the buffer tank 41. The fourth channel 24 is configured as, for example, a resin tube or a cylindrical member such as a metal or glass pipe. Hereinafter, a portion of the fourth channel 24 located between the buffer tank 41 and the fifth channel 25 will also be referred to as "fourth channel 24A", as appropriate. Also, a portion of the fourth channel 24 located between the buffer tank 40 and the fifth channel 25 will also be referred to as "fourth channel 24B", as appropriate.

The fifth channel 25 couples the fourth channel 24 and the outside of the sensor module 1A. For example, one end of the fifth channel 25 extends to the outside of the housing. An exhaust port that opens to the outside may be provided to one end of the fifth channel 25. The other end of the fifth channel 25 is joined to a portion of the fourth channel 24.

The valve 70 is installed to the third channel 23. The valve 70 is in a closed state during the detection process of the sensor module 1A. The valve 70 is in an open state during the refresh process of the sensor module 1A. When the valve 70 opens during the refresh process of the sensor module 1A, a portion of the second fluid having flowed into the inlet 21A is sent to the buffer tank 40 via the third channel 23. By sending the second fluid to the buffer tank 40, the first fluid remaining in the buffer tank 40 is discharged to the fourth channel 24B side. The valve 70 may be configured as an electrostatically-driven semiconductor valve or an electromagnetically-driven valve.

The valve 71 is installed to the fourth channel 24. The valve 71 is in a closed state during the detection process of the sensor module 1A. The valve 71 is in an open state during the refresh process of the sensor module 1A. When the valve 71 opens during the refresh process of the sensor module 1A, the first fluid remaining in the buffer tank 40 is discharged to the fifth channel 25 via the fourth channel 24B. The valve 71 may be configured as an electrostatically-driven semiconductor valve or an electromagnetically-driven valve.

The valve 72 is installed to the inlet 20A of the first channel 20. The valve 72 is in an open state during the detection process of the sensor module 1A. The valve 72 is in a closed state during the refresh process of the sensor module 1A. The valve 72 is closed during operation by the discharge unit 80 in the refresh process of the sensor module 1A. Because the valve 72 is closed during operation by the discharge unit 80 in the refresh process of the sensor module 1A, the first fluid is prevented from newly mixing into the buffer tank 40 from the inlet 20A. The valve 72 may be configured as an electrostatically-driven semiconductor valve or an electromagnetically-driven valve.

The discharge unit 80 is installed to the fifth channel 25. During the refresh process of the sensor module 1A, the discharge unit 80 discharges the first fluid in the buffer tank 40 to the outside of the sensor module 1A via the fourth channel 24B and the fifth channel 25. During the refresh process of the sensor module 1A, also, the discharge unit 80 discharges the second fluid in the buffer tank 41 to the outside of the sensor module 1A via the fourth channel 24A and the fifth channel 25.

The discharge unit 80 is configured as, for example, a piezoelectric pump. The discharge unit 80 may have a larger flow rate than, for example, the first supply unit 50 and the second supply unit 51. By increasing the flow rate of the discharge unit 80, the time necessary for the refresh process of the sensor module 1A can be reduced.

Figure 5:
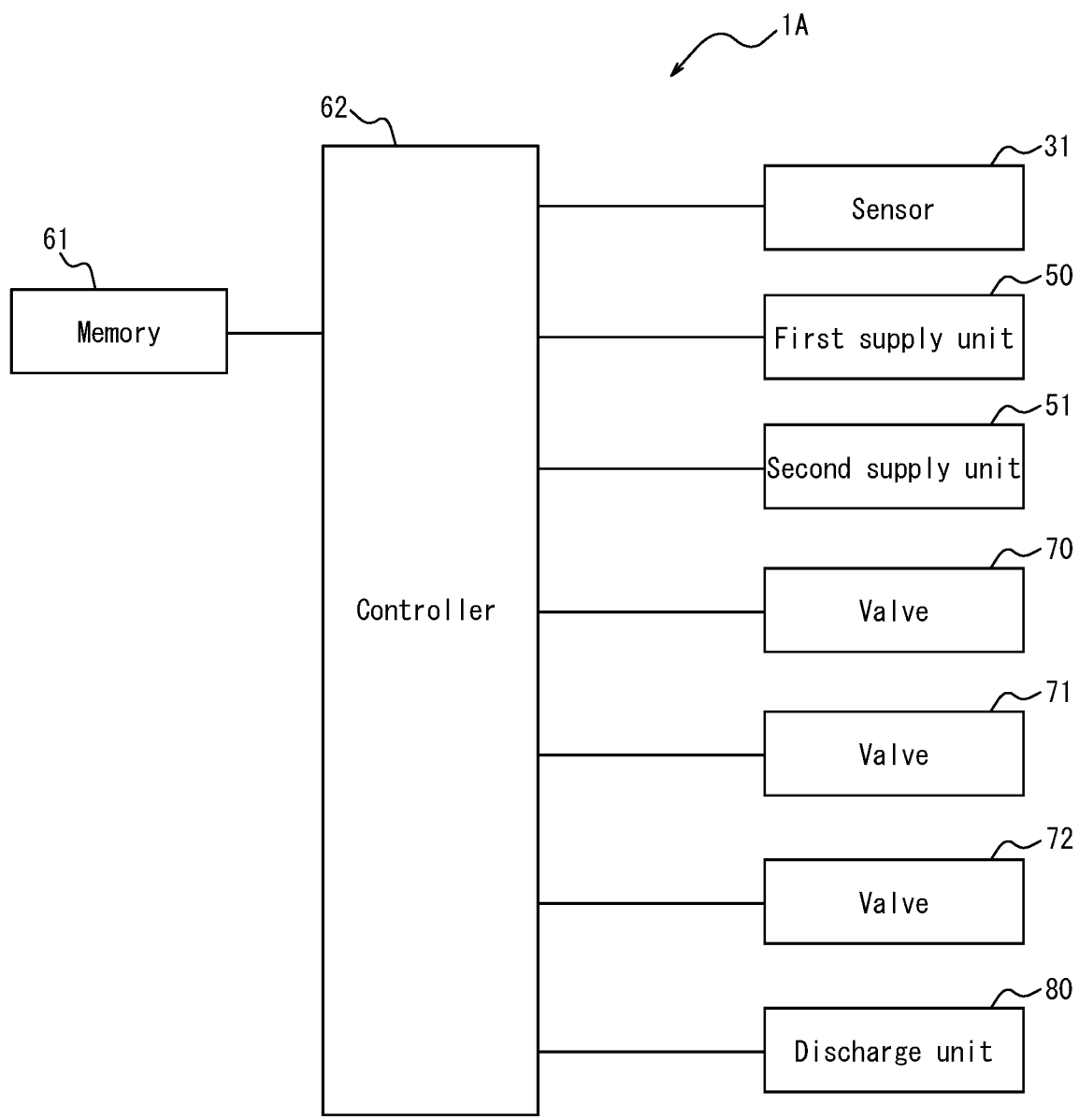
FIG. 5 is a functional block diagram illustrating a schematic configuration of the sensor module of FIG. 4.

FIG. 5 is a functional block diagram illustrating a schematic configuration of the sensor module 1A of FIG. 4. The constituent elements illustrated in FIG. 5 the same as those illustrated in FIG. 2 are denoted by the same reference signs, and descriptions thereof will be omitted.

The sensor module 1A includes the sensor 31, the first supply unit 50, the second supply unit 51, the memory 61, the controller 62, the valve 70, the valve 71, the valve 72, and the discharge unit 80.

The controller 62 controls the valves 70, 71, 72 and the discharge unit 80. During the detection process of the sensor module 1A, the controller 62 controls so as to close the valves 70 and 71 and open the valve 72. During the refresh process of the sensor module 1A, the controller 62 controls so as to open the valves 70 and 71.

When the valve 70 opens during the refresh process of the sensor module 1A, a portion of the second fluid flowing into the inlet 21A illustrated in FIG. 4 is sent to the buffer tank 40 via the third channel 23. By sending the second fluid to the buffer tank 40, the first fluid remaining in the buffer tank 40 is discharged to the fourth channel 24. Further, when the valve 71 opens, the first fluid discharged from the buffer tank 40 by the second fluid is sent to the fifth channel 25 via the fourth channel 24B.

During the refresh process of the sensor module 1A, the controller 62 further controls the discharge unit 80. The controller 62 causes the discharge unit 80 to discharge the first fluid in the buffer tank 40 illustrated in FIG. 4 to the outside of the sensor module 1A via the fourth channel 24B and the fifth channel 25. Also, the controller 62 causes the discharge unit 80 to discharge the second fluid in the buffer tank 41 illustrated in FIG. 4 to the outside of the sensor module 1A via the fourth channel 24A and the fifth channel 25. Further, the controller 62 controls so as to close the valve 72 during operation by the discharge unit 80. Because the valve 72 is closed, the first fluid is suppressed from newly mixing into the buffer tank 40 from the inlet 20A.

In the sensor module 1A according to the second embodiment, as described above, the third channel 23 couples the inlet 21A and the buffer tank 40. This configuration can send the second fluid to the buffer tank 40 via the third channel 23 during the refresh process of the sensor module 1A. By sending the second fluid to the buffer tank 40, the first fluid can be discharged from the buffer tank 40. By discharging the first fluid from the buffer tank 40 in the refresh process, the measurement accuracy of the detection target substance by the sensor module 1A can be improved.

In the sensor module 1A according to the second embodiment, further, the fourth channel 24 couples the buffer tank 40 for the first fluid and the buffer tank 41 for the second fluid. In the sensor module 1A according to the present embodiment, also, the fifth channel 25 couples the fourth channel 24 and the outside. This configuration can discharge the first fluid remaining within the buffer tank 40 to the outside of the sensor module 1A via the fourth channel 24B and the fifth channel 25 by the discharge unit 80. This configuration can also discharge the second fluid in the buffer tank 41 to the outside of the sensor module 1A via the fourth channel 24A and the fifth channel 25 by the discharge unit 80. Thus, the time necessary for the refresh process of the sensor module 1A may be reduced, as will be described below.

As a comparative example, a case in which the first fluid remaining within the buffer tank 40 is discharged by flowing the second fluid from the inlet 20A illustrated in FIG. 4 will be assumed. In this case, the first fluid remaining within the buffer tank 40 is discharged to the passage 20B by the second fluid from the inlet 20A. Further, the first fluid from the buffer tank 40 is discharged to the outside from the discharge path 22 by the first supply unit 50. Here, the flow rate of the first supply unit 50 is often set to be somewhat small, in order to enable a finer control in the detection process. Thus, performing the refresh process using the first supply unit 50 in the manner of the comparative example may take time.

In the present embodiment, on the other hand, the discharge unit 80 which is mainly used for the refresh process executes the refresh process of the sensor module 1A. Because the discharge unit 80 is mainly used for the refresh process, the flow rate may be designed to be larger than the first supply unit 50 or the like. In the present embodiment, accordingly, the time necessary for the refresh process of the sensor module 1A can be reduced.

Although the disclosure has been described based on the figures and the embodiments, it is to be understood that various changes and modifications may be implemented based on the present disclosure by those who are ordinarily skilled in the art. Accordingly, such changes and modifications are included in the scope of the disclosure herein. For example, functions and the like included in each functional unit, each means, and the like may be rearranged without logical inconsistency, so as to combine a plurality of units or steps together or to subdivide them. Also, each of the above embodiments does not need to be practiced strictly following the description thereof, and may be implemented by appropriately combining or partially omitting the features.

For example, another detection mechanism may be used for the chamber 30 in place of the sensor 31. Such a detection mechanism may include, for example, a semiconductor sensor, a catalytic combustion sensor, an electrochemical sensor, an optical sensor, a SAW sensor, or a QCM sensor.

The invention claimed is:

1. A sensor module comprising:
   a sensor configured to detect a specific substance in a sample;
   a single chamber configured to include the sensor;
   a first channel configured to supply a first fluid as the sample to the sensor;
   a second channel configured to supply a second fluid different from the first fluid to the sensor; and
   a single outlet configured to discharge exhaust from the single chamber, the single outlet being directly connected to the single chamber,
   wherein the first channel includes a first fluid buffer tank configured to hold the first fluid for a fixed time interval,
   wherein the sensor module further comprises a third channel that fluidly couples the second channel and the first fluid buffer tank.

2. The sensor module according to claim 1,
   wherein the second channel includes a second fluid buffer tank configured to hold the second fluid for a fixed time interval.

3. The sensor module according to claim 2,
   wherein the second channel further includes an inlet for flowing the second fluid into the second fluid buffer tank from an outside, and
   the third channel is joined to the inlet.

4. The sensor module according to claim 3, further comprising:
   a fourth channel that couples the first fluid buffer tank and the second fluid buffer tank; and
   a fifth channel that couples the fourth channel and an outside.

5. The sensor module according to claim 2, further comprising:
   a fourth channel that couples the first fluid buffer tank and the second fluid buffer tank; and
   a fifth channel that couples the fourth channel and an outside.

6. The sensor module according to claim 2, further comprising:
   a fourth channel that couples the first fluid buffer tank and the second fluid buffer tank; and
   a fifth channel that couples the fourth channel and an outside.

7. The sensor module according to claim 2, wherein the first fluid is supplied to the first fluid buffer tank and the second fluid different from the first fluid is supplied to the second fluid buffer tank, respectively.

8. The sensor module according to claim 2, wherein the first fluid buffer tank and the second fluid buffer tank are connected to the single chamber.

9. The sensor module according to claim 1, wherein the third fluid channel couples the second channel and the first fluid buffer tank without passing through the first channel.

10. The sensor module according to claim 1, wherein the first fluid supplied to the first fluid buffer tank and the second fluid are supplied from different sources.

11. The sensor module according to claim 1, wherein the second channel is configured to supply the second fluid different from the sample to the sensor.

* * * * *